US008715364B2

(12) United States Patent
Ernsberger (10) Patent No.: US 8,715,364 B2
(45) Date of Patent: May 6, 2014

(54) ASPHERIC HIP BEARING COUPLE (75) Inventor: Craig N. Ernsberger, Granger, IN (US)

(73) Assignee: DePuy Synthes Products, LLC, Raynham, MA (US)

( * ) Notice: Subject to any disclaimer, the term of this patent is extended or adjusted under 35 U.S.C. 154(b) by 1230 days.

(21) Appl. No.: 11/702,303

(22) Filed: Feb. 5, 2007

(65) Prior Publication Data

US 2008/0188944 A1    Aug. 7, 2008

(51) Int. Cl.
*A61F 2/32* (2006.01)
(52) U.S. Cl.
USPC ..................................... 623/22.15; 623/23.4
(58) Field of Classification Search
USPC ............... 623/22.15, 22.4, 23.39, 22.21, 23.4
See application file for complete search history.

(56) References Cited

U.S. PATENT DOCUMENTS

| | | | |
|---|---|---|---|
| 3,510,883 A | 5/1970 | Cathcart, III | |
| 3,521,302 A | 7/1970 | Müller | |
| 4,031,570 A | 6/1977 | Frey | |
| 4,784,662 A | 11/1988 | Müller | |
| 4,840,632 A | 6/1989 | Kampner | |
| 4,911,723 A * | 3/1990 | Menschik | 623/22.15 |
| 5,383,936 A * | 1/1995 | Kubein-Meesenburg et al. | 623/19.13 |
| 5,443,519 A | 8/1995 | Averill et al. | |
| 5,549,690 A | 8/1996 | Hollister et al. | |
| 5,549,693 A * | 8/1996 | Roux et al. | 623/22.14 |
| 5,609,643 A | 3/1997 | Colleran et al. | |
| 5,641,323 A | 6/1997 | Caldarise | |
| 5,879,405 A | 3/1999 | Ries et al. | |
| 5,879,406 A * | 3/1999 | Lilley | 623/22.15 |
| 5,928,285 A | 7/1999 | Bigliani et al. | |
| 5,972,032 A | 10/1999 | Lopez et al. | |
| 6,013,103 A | 1/2000 | Kaufman et al. | |
| 6,059,830 A | 5/2000 | Lippincott, III et al. | |

(Continued)

FOREIGN PATENT DOCUMENTS

DE        4428290 A1     2/1996
DE        19915814       10/2000

(Continued)

OTHER PUBLICATIONS

Bergmann, G. et al., "Hip Contact Forces and Gait Patterns from Routine Activities", Journal of Biomechanics, 34, 859-871, (13 pages).

(Continued)

*Primary Examiner* — Bruce E Snow
*Assistant Examiner* — Melissa Hoban
(74) *Attorney, Agent, or Firm* — Maginot, Moore & Beck LLP (57) ABSTRACT

A joint prosthesis device comprises a head configured to fit within a cup. The cup includes a concave cup surface defined by at least one radius of curvature $R_C$. The head includes a convex head surface defined by at least one radius of curvature $R_H$. The convex head surface is configured to engage the concave cup surface. The convex head surface provides an articulation zone where the head surface engages the cup surface. $R_C$ differs from $R_H$ in the articulation zone by a first amount. The convex head surface also provide a peripheral zone outside of the articulation zone. $R_C$ differs from $R_H$ in the peripheral zone by a second amount that is greater than the first amount. The peripheral zone generally extends over an area subtended by a minimum angle having a vertex at a center of the head.

20 Claims, 9 Drawing Sheets

(56) References Cited

U.S. PATENT DOCUMENTS

| | | |
|---|---|---|
| 6,126,695 A * | 10/2000 | Semlitsch .................. 623/22.15 |
| 6,660,040 B2 | 12/2003 | Chan et al. |
| 6,706,068 B2 | 3/2004 | Ferree |
| 2004/0225370 A1* | 11/2004 | Cruchet et al. ............. 623/22.18 |
| 2005/0087047 A1 | 4/2005 | Farrar |
| 2005/0256584 A1* | 11/2005 | Farrar ........................ 623/22.15 |
| 2007/0073410 A1 | 3/2007 | Raugel |
| 2008/0114459 A1 | 5/2008 | Scott et al. |
| 2010/0063589 A1 | 3/2010 | Tepic |

FOREIGN PATENT DOCUMENTS

| | | |
|---|---|---|
| DE | 19915814 A1 * | 10/2000 |
| EP | 0226762 A1 | 7/1987 |
| EP | 0302850 A2 | 2/1989 |
| EP | 0648478 A2 | 4/1995 |
| EP | 0681815 A1 | 11/1995 |
| EP | 0841041 A2 | 5/1998 |
| EP | 0748193 B1 | 12/2001 |
| EP | 0841041 B1 | 9/2002 |
| EP | 1340477 A2 | 9/2003 |
| EP | 1442725 A2 | 8/2004 |
| EP | 1337204 B1 | 4/2005 |
| EP | 1598033 A1 * | 11/2005 |
| EP | 1465557 B1 | 10/2006 |
| EP | 1767171 A1 | 3/2007 |
| EP | 1 337 204 | 8/2007 |
| EP | 1952786 A2 | 8/2008 |
| EP | 1767171 B1 | 12/2008 |
| FR | 2134170 A1 | 12/1972 |
| GB | 2366733 A | 4/1998 |
| GB | 2366733 A | 3/2002 |
| WO | WO 95/23566 | 9/1995 |
| WO | 9716138 | 5/1997 |
| WO | WO 02/43626 | 6/2002 |
| WO | 03061532 A1 | 7/2003 |
| WO | WO 2008/015287 | 2/2008 |

OTHER PUBLICATIONS

European Search Report of European Application No. EP 08 25 0408.
European Search Report in corresponding EP application (i.e., EP 08 17 1397) completed May 11, 2009 (2 pages).
Anderson, Andrew Edward, "Computational Modeling of Hip Joint Mechanics," (Apr. 2007) (unpublished Ph.D. dissertation, The University of Utah), (available on the web at mrl.sci.utah.edu/mrl/papers/Dissertation_AEA.pdf) (34 pages).
Cilingir et al, "Three-Dimensional Anatomic Finite Element Modeling of Hemi-Arthroplasty of Human Hip Joint," Trends in Biomaterials and Artificial Organs, vol. 21(1), pp. 63-72, 2007, (10 pages).
Hurwitz et al., "A new parametric approach for modeling hip forces during gait," Journal of Biomechanics, 2003, pp. 113-119, vol. 36, Elsevier, USA (7 pages).
McKellop, Ph.D. et al., "In Vivo Wear of 3 Types of Metal on Metal Hip Prostheses During 2 Decades of Use," Clinical Orthopaedics and Related Research, No. 329S, pp. S128-S140, © 1996 Lippincott-Raven Publishers, (13 pages).
Morlock et al., "Duration and frequency of every day activities in total hip patients," Journal of Biomechanics, 2001, pp. 873-881, vol. 34, Elsevier, USA (9 pages).
Reinbolt et al., "Determination of patient-specific multi-joint kinematic models through two-level optimization," Journal of Biomechanics, 2005, pp. 621-626, vol. 38, Elsevier, USA (6 pages).
Sbarbaro, Jr., "The Sbarbaro Total Hip," published at least as early as Feb. 4, 2007 (1 page).
McKee et al., "The McKee-Farrar Total Hip," published at least as early as Feb. 4, 2007 (1 page).
European Search Report in corresponding European patent application (i.e., EP08250408.5), dated Dec. 29, 2009 (4 pages).

* cited by examiner

FIG. 9

# ASPHERIC HIP BEARING COUPLE

FIELD

This application relates to the field of prosthetic devices, and particularly joint prostheses comprising head and cup arrangements.

BACKGROUND

A common orthopedic joint prosthesis includes a ball and cup arrangement. For example, hip joints typically comprise a rounded femoral head and an acetabular cup. The rounded femoral head is provided on a stem that is configured to engage the intramedullary cavity of the femur and secure the head on the femur. The rounded femoral head includes a convex surface configured to engage a concave surface on the acetabular cup. The acetabular cup is configured for implantation on the acetabulum of the pelvis. When the rounded femoral head is received within the acetabular cup, a ball and socket joint is provided.

In order to reduce wear between the components of the joint prosthesis, the components are manufactured such that the clearance between the bearing surfaces is minimized. The term "clearance" is often used in reference to a "diametral clearance" of the joint prosthesis. The diametral clearance between bearing surfaces is generally considered to be the difference in the diameter defining the bearing surface of the ball and the diameter defining the bearing surface of the cup.

While minimal diametral clearance between the bearing surfaces is desired, at least two factors limit the reduction of clearances. First, manufacturing tolerances generally limit the extent to which clearances may be reduced. For example, for diametral clearances below the 15-30 micron range, it has been observed that imperfect formation of the femoral head and the acetabular cup contributes to local interferences and small deformations that result in wear.

Second, acetabular cup deformation during implantation into the acetabulum also limits the degree to which clearances may be reduced in a hip joint prosthesis. This deformation generally occurs near the equatorial lip of the acetabular cup. For substantially spherical cup and head arrangements, reduction in clearances near the pole of the head also means reduction in clearances near the equatorial lip. In other words, when the head and the cup of a hip prosthesis are substantially spherical, the small clearances near the pole of the head are also found in the region near the equatorial lip of the cup. Thus, when cup deformation occurs near the equatorial lip in a low clearance spherical deign, interference is likely to occur between the equatorial lip of the cup and the ball.

One way to reduce clearance complications resulting from acetabular cup deformation is to provide a conformal region having a small clearance near the center of the primary articulation area of the femoral head, and a peripheral region surrounding the conformal region, wherein the peripheral region has a significantly greater clearance than the conformal region, including a significantly greater clearance near the lip of the cup. With this arrangement, deformations near the equatorial lip of the acetabular cup are less likely to result in obstruction with the femoral head because of the increased clearance near the equatorial lip. Although several of these arrangements have been provided in the past, they have not provided optimal solutions. In particular, many of these arrangements include peripheral regions surrounding the conformal region where the clearances in these peripheral regions quickly diverge from the relatively small clearances in the conformal zone. However, when the clearance in the peripheral region is too great, significant wear may result.

Accordingly, what is needed is a joint prosthesis configured to avoid interference between the ball and cup even if the equatorial region of the cup is deformed during implantation. It would also be advantageous if the clearance between the ball and cup could remain relatively low even in a peripheral region surrounding the conformal region.

SUMMARY

A joint prosthesis device comprises a head configured to fit within a cup. The cup includes a concave cup surface defined by at least one radius of curvature $R_C$. The head includes a convex head surface defined by at least one radius of curvature $R_H$. The convex head surface is configured to engage the concave cup surface. The convex head surface provides an articulation zone where the head surface engages the cup surface. In one embodiment, $R_C$ differs from $R_H$ in the articulation zone by a first amount that is no greater than forty microns. The convex head surface also provides a peripheral zone outside of the articulation zone. $R_C$ differs from $R_H$ in the peripheral zone by a second amount that is greater than the first amount but is no greater than fifty microns. The peripheral zone generally extends over an area subtended by an angle of at least 10°, the angle having a vertex at a center of the head.

In at least one embodiment, the peripheral zone includes a transition zone and an equatorial zone. The equatorial zone is provided in proximity of a region of the head opposing the lip of the acetabular cup and the transition zone lies between the equatorial zone and the articulation zone. In such embodiment, the clearance in the transition zone is generally greater than the clearance in the articulation zone. Furthermore, the clearance in the equatorial zone is generally greater than the clearance in the transition zone. In one embodiment, the clearance in the transition zone gradually increases moving from the perimeter of the articulation zone to the perimeter of the equatorial zone. In another embodiment, the clearance in the transition zone remains substantially constant in both the transition zone and the equatorial zone.

The above described features and advantages, as well as others, will become more readily apparent to those of ordinary skill in the art by reference to the following detailed description and accompanying drawings.

DESCRIPTION

Figure 1:
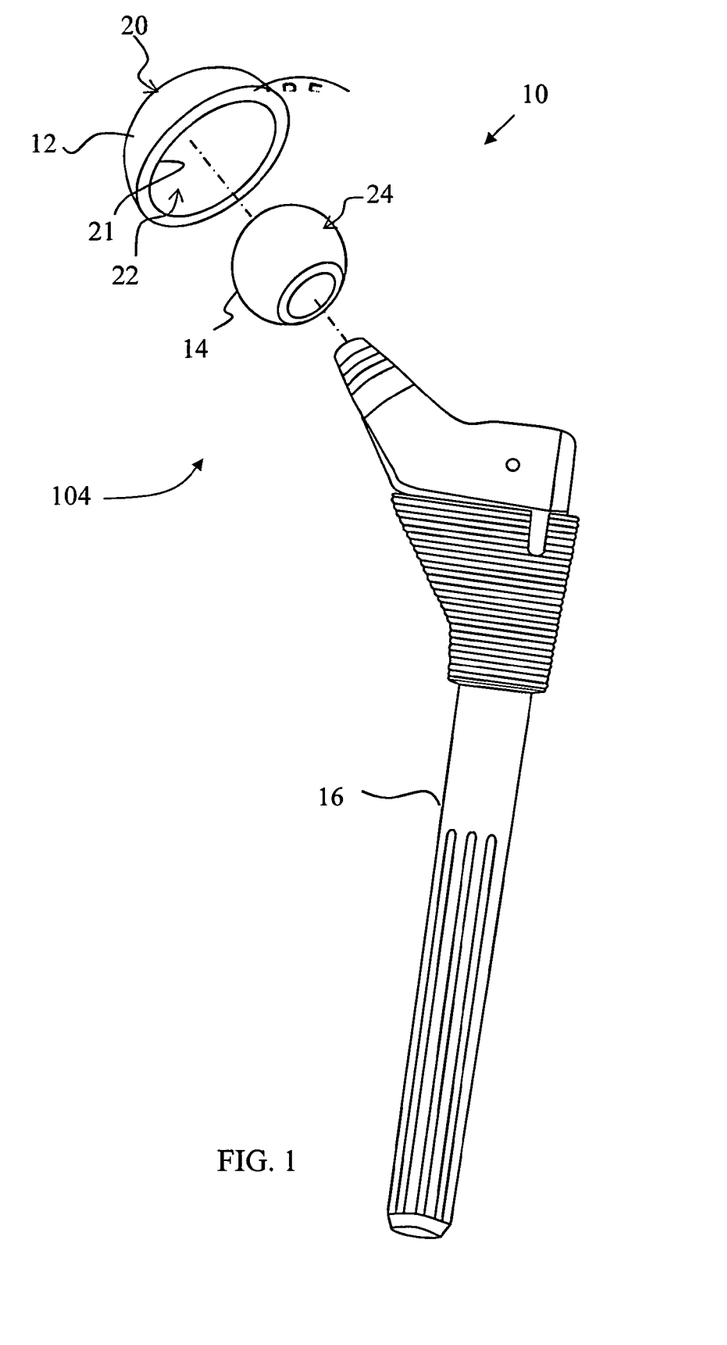
FIG. 1 shows a perspective view of various components of a hip prosthesis including an acetabular cup, a femoral head, and a femoral stem.

With reference to FIG. 1, a prosthetic device in the form of a prosthetic hip joint 10 is shown in a disassembled configuration. The prosthetic hip joint comprises an acetabular cup 12, a femoral head 14 (or "ball"), and a femoral stem 16. The femoral head 14 is configured for attachment to the femoral stem 16. The femoral head 14 is also configured to slideably engage the acetabular cup 12.

The acetabular cup 12 is the part of the prosthetic hip joint 10 that forms the socket of a ball-and-socket structure. The acetabular cup 12 includes a convex outer surface 20 configured for engagement with a patient's acetabulum and a concave interior surface 22 configured to engage the femoral head 14. The cup 12 includes a lip 21 which defines a rim in a peripheral region where the convex outer surface 20 meets the concave interior surface 22. A vertex 33 is provided upon the concave interior surface 22 of the cup 12. The vertex 33 is generally the point on the cup 12 that is at the peak of the concave interior surface and equidistant from all points on the lip 21. The convex outer surface 20 of the acetabular cup 12 is provided as part of a shell comprised of a biocompatible material. In at least one embodiment, the shell is comprised of a relatively rigid material, such as a biocompatible metal or ceramic. For example, the shell may be comprised of titanium or cobalt chrome. The concave interior surface 22 of the cup 12 comprises a liner that provides a bearing surface for the acetabular cup. The liner may be comprised of a biocompatible material that offers a low coefficient of friction, such as polyethylene. Alternatively, the liner may be comprised of a metal or ceramic. While exemplary materials for the acetabular cup have been offered herein, one of skill in the art will recognize that numerous other biocompatible materials may be used as are known in the art.

The femoral component which includes the femoral stem 16 and the femoral head 14 replaces the natural head of the femur. The femoral head 14 includes a ball-shaped member that provides a convex outer surface 24 designed and dimensioned to be received by the concave interior surface 22 of the acetabular cup 12. The femoral head 14 is fixed to the femoral stem 16. The femoral head 14 and femoral stem are comprised of a relatively rigid biocompatible material such as a ceramic or metal. For example, the ball may be comprised of cobalt chrome or stainless steel. While exemplary materials for the femoral component have been offered herein, one of skill in the art will recognize that numerous other biocompatible materials may be used as are known in the art.

Figure 2:
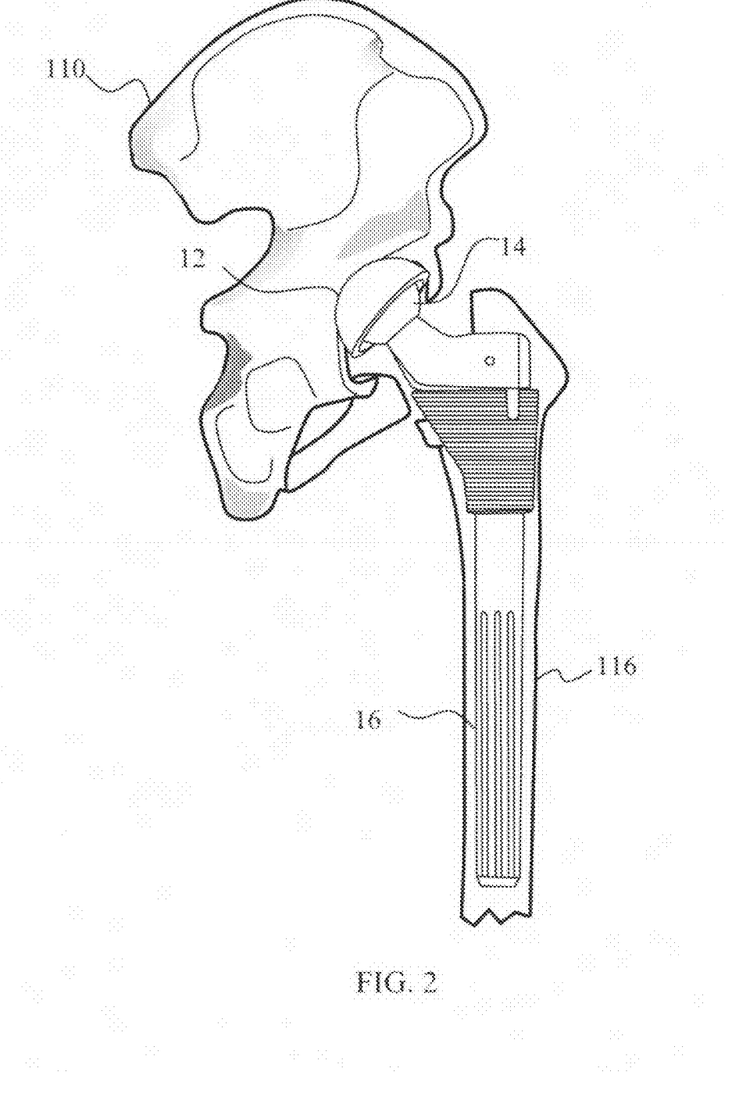
FIG. 2 shows a cutaway view of the hip prosthesis of FIG. 1 assembled and implanted in a pelvis and femur.

As shown in FIG. 2, the prosthetic hip joint 10 may be implanted in a patient by securing the acetabular cup 12 in the acetabulum 112 of the pelvis 110. Also, the femoral component is secured to the femur by inserting the femoral stem 16 in the intramedullary cavity of the femur 116. The femoral head 14 which protrudes from the femoral stem 16 is brought into slideable contact with the acetabular cup 12 such that the femoral head 14 is allowed to rotate within the acetabular cup 12. This slideable relationship provides for a ball and socket type joint.

Figure 3:
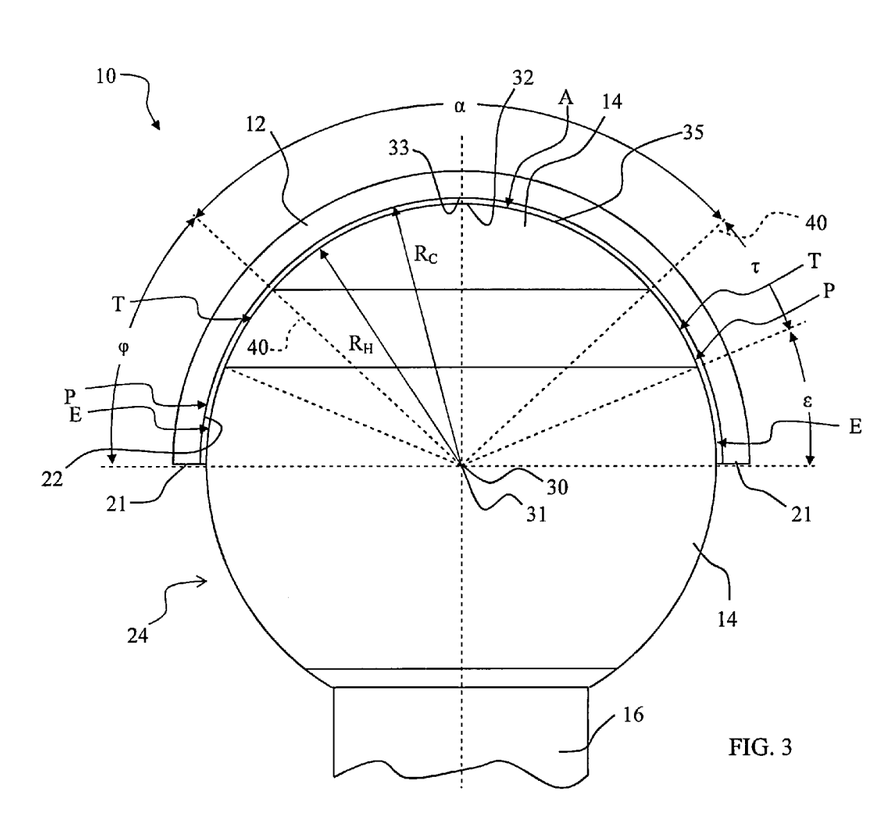
FIG. 3 shows a cross-sectional view of the femoral head and acetabular cup of FIG. 1.

With reference now to FIG. 3, an enlarged cross-sectional view is shown of the configuration of the acetabular cup 12 in relation to the femoral head 14, with the head 14 slightly removed from engagement with the cup 12. The configuration of the head 14 defines different zones or regions for the prosthesis, including an articulation zone A and a peripheral zone P.

The term "articulation zone" as used herein refers to a region of the head 14 which provides a main contact area for engagement between the head 14 and the cup 12 for nearly all joint movements once implanted in a patient. Accordingly, with reference to FIG. 3, the concave bearing surface 22 of the cup 12 slides upon the convex bearing surface 24 of the head 14 primarily within the articulation zone A, and contact between the ball 14 and cup 12 occurs in this articulation zone A for nearly all joint movements. However, contact between the head 14 and cup 12 is not entirely limited to the articulation zone, as there will be certain extra-ordinary movements by the patient where contact between the ball 14 and cup 12 will occur outside of the articulation zone A. Thus, the term "articulation zone" does not include any region of the ball 14 that may come into contact with cup 12 at any time, but refers to that zone of the ball 14 which provides the primary contact area for engagement with the cup 12.

In the embodiment of FIG. 3, the articulation zone A is shown as lying within the region subtended by the angle a having a vertex at the center of the head. This means that the articulation zone A is provided within a perimeter defined by the intersection of a right circular cone (represented by dotted lines 40) with the convex outer surface 24 of the head 14, the cone 40 having an apex 31 at the center 30 of the head 14 and an aperture (or "opening angle") of $\alpha$. In the embodiment of FIG. 3, the cone 40 is symmetric about the pole 32 of the head 14. The angle $\alpha$ is generally less than 145°, and typically between 85° and 105°. In at least one embodiment, the angle a is about 95°.

The acetabular cup 12 is shown in the embodiment of FIG. 3 centered upon and symmetric with respect to the pole 32 of the head 14 in the coronal plane. In particular, the vertex 33 of the concave bearing surface 22 of the cup 12 is shown in FIG. 3 aligned with the pole 32 of the head 14. When the cup 12 is in this position relative to the head 14, it is considered to be in a centered position. In practice, it will be recognized that the cup 12 and head 14 are generally aligned in the implanted position such that the vertex 33 of the cup is about thirty degrees off the pole 32 of the head in the coronal plane and about fifteen degrees off the pole of the head in the sagital plane. For a spherical cup geometry, the articulation area on the head is independent of the cup orientation.

The region outside of the articulation zone A on the head 14 is generally referred to herein as the peripheral zone or peripheral region P. The peripheral zone P is shown in FIG. 3 as subtended by the angle $\phi$ having a vertex at the center 30 of the head. Accordingly, for an aspheric head of symmetrical design, the peripheral zone P includes that portion of the convex head surface 24 defined when an arc subtended by the angle $\phi$ is rotated about the axis passing through the pole 32 and the center 30 of the head.

In the embodiment of FIG. 3, the peripheral zone P is adjacent to the articulation zone A. Thus, the peripheral zone P lies outside of the articulation zone and extends from the perimeter of the articulation zone A to a portion of the head 14 removed from the articulation zone and at least to such portions of the head that are generally opposed to the lip 21 of the acetabular cup 12. In the embodiment of FIG. 3, the angle φ which defines the boundaries of the peripheral zone P, is shown as being equal to ½(180°−α). The angle φ defining the peripheral zone P is generally between 10° and 70°, depending upon the particular configuration of the prosthesis joint 10.

In the embodiment of FIG. 3, the peripheral zone P is comprised of two different zones or sub-regions. These two sub-regions include the transition zone T and the equatorial zone E, both of which are centered about the pole 32 in an aspheric symmetric design. The equatorial zone E is the zone provided on the head 14 which includes the portion of the head nearest the lip 21 of the acetabular cup 12. In particular, the equatorial zone E includes those portions of the convex outer surface 24 of the head 14 in FIG. 3 subtending the angle ϵ having a vertex at the center 30 of the head 14. The angle ϵ is generally less than 50° and typically at least 10°. In the embodiment of FIG. 3, the equatorial zone E extends to the equator of the head.

The transition zone T is the region lying between the articulation zone A and the equatorial zone E. The transition zone T includes those portions of the convex outer surface 24 of the head 14 subtending the angle τ in FIG. 3. The angle τ is generally less than 40° and typically at least 10°. As set forth in further detail below, the clearance between the bearing surfaces of the acetabular cup 12 and the femoral head 14 transition in this zone T from the smaller clearance of the articulation zone to the larger clearance of the equatorial zone E. Furthermore, the clearance in the transition zone T may be constant or may vary when moving from the articulation zone A to the equatorial zone E.

With continued reference to FIG. 3, the head 14 is defined by a radius of curvature, $R_H$, which extends from a center 30 of the head 14 to the convex surface 24 of the head. In at least one embodiment, the head 14 does not form a perfect sphere, and the radius of curvature $R_H$ is different at different points on the surface 24 of the sphere. In this embodiment, the radius of curvature $R_H$ is different in each of the different regions of the head. For example, the radius of curvature $R_H$ of the head 14 may be larger in the articulation zone A than in the peripheral zone P. Furthermore, the radius of curvature $R_H$ of the head may be larger in the transition zone T than in the equatorial zone E.

Similar to the head 14, the acetabular cup 12 is also defined by a radius of curvature $R_C$. The radius of curvature $R_C$ extends from the virtual center of the cup 12 to the concave inner surface 22 of the acetabular cup 12. In at least one embodiment, the radius of curvature $R_C$ is constant at all points on the concave inner surface 22 such that the concave inner surface 22 of the cup is spherical. In another embodiment, the radius of curvature $R_C$ is different at different points on the concave inner surface 22, and in different regions. For example, the radius of curvature $R_C$ of the cup may be smaller at those points opposing the articulation zone A than at those points opposing the peripheral zone P. Furthermore, the radius of curvature $R_C$ of the cup 12 may be smaller at those points opposing the transition zone T than at those points opposing the equatorial zone E.

The difference between $R_C$ and $R_H$ at a given point on the head 14 and the opposing point on the cup 12 (i.e., on a given ray extending from the center of the head to the concave surface 22 of the cup) defines half the diametral clearance at that location. The term "radial clearance" as used herein refers to half the diametral clearance. Accordingly, a "radial clearance" may be calculated as either $R_C$-$R_H$ or $R_H$-$R_C$. When reference is made herein to a radial clearance in a given zone (i.e., the articulation zone, the transition zone or the equatorial zone), such radial clearance refers to the difference between $R_H$ and $R_C$ along a ray extending from the center 30 of the head 14 and passing through such zone, with the cup 12 in an equilibrium position with respect to the head 14. In at least one embodiment of the prosthetic device, the radial clearance in the articulation zone A is no more than forty microns and the radial clearance in the peripheral zone P is no greater than fifty microns. For example, in one embodiment the radial clearance in the articulation zone A is about thirty microns and the radial clearance in the equatorial zone E is about forty microns. In the transition zone T lying between the articulation zone and the equatorial zone, the radial clearance may gradually increase from thirty microns to forty microns moving from the perimeter of the articulation zone to the perimeter of the equatorial zone. Alternatively, the transition zone T may provide a generally uniform radial clearance, such as thirty-five microns, which lies between the thirty micron radial clearance in the articulation zone A and the forty micron radial clearance in the equatorial zone E. Although exemplary radial clearances have been provided with reference to FIG. 3, one of skill in the art will recognize that numerous other clearances are possible.

Figure 4:
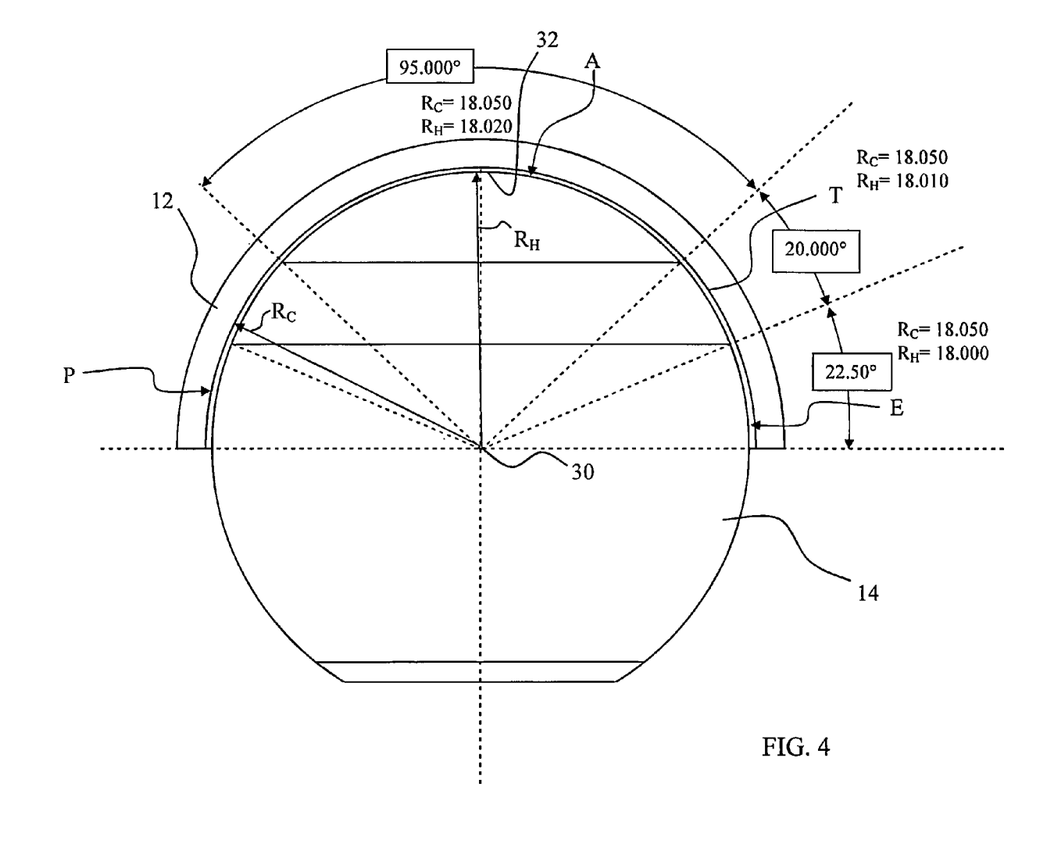
FIG. 4 shows an exemplary embodiment of the femoral head and cup arrangement of FIG. 3 wherein the concave surface of the acetabular cup is spherical and the radius of curvature of the femoral head changes from zone to zone.

FIG. 4 shows an exemplary embodiment of a head 14 with an aspheric surface 24. The head 14 of FIG. 4 is configured for use with a cup 12 having a generally spherical concave surface 22. Accordingly, the radius of curvature $R_C$ of the cup 12 is represented in FIG. 4 as being the same in the articulation zone A, the transition zone T, and the equatorial zone E. In particular, the radius of curvature $R_C$ in FIG. 4 is shown as a constant 18.050 mm in FIG. 4 from zone to zone. Conversely, the head 14 is aspherical with the radius of curvature $R_H$ decreasing when moving from the articulation zone A to the transition zone T and to the equatorial zone E. In particular, the radius of curvature $R_H$ is about 18.020 mm in the articulation zone A, about 18.010 mm in the transition zone T, and about 18.000 mm in the equatorial zone. With this arrangement, the aspherical head is designed and dimensioned to fit within the substantially spherical cup with radial clearances generally no greater than fifty microns. In particular, the radial clearance in the articulation zone A is about thirty microns, the radial clearance in the transition zone is about forty microns, and the radial clearance in the equatorial zone is about fifty microns. While exemplary radii of curvature are provided herein, it will be understood by one of skill in the art that the concave surface of the cup 12 and the convex surface of the head 14 desirably have certain maximum surface roughnesses, and it will be understood that the radii $R_C$ and $R_H$ are measured to the surfaces of the ball and cup as defined by the tips of the surface asperities as measured by one of several standard coordinate measuring devices, as are known to those of skill in the art.

In the embodiment of FIG. 4, the articulation zone A has been defined within a cone having an apex at the center 30 of the head 14, a 95° aperture, and symmetric about the pole 32. In vivo, it has been observed that a typical prosthesis articulation zone which results from various daily living activities may be defined by a 45° aperture cone having an apex at the center 30 and symmetric about a point on the femoral head surface that is about 25° lateral from the pole 32 (such cone hereinafter referred to as an "exemplary in-vivo articulation zone"). In FIG. 4, the prosthesis articulation zone A is sufficient in size to include the exemplary in-vivo articulation zone within the boundaries of the prosthesis articulation zone A. Accordingly, the embodiment of FIG. 4 provides a head 14 having an aspheric yet symmetric outer surface 24. The symmetric design of the head 14 allows it to be secured to the femoral stem such that the prosthesis articulation zone will cover the exemplary in-vivo articulation zone without concern for degree of rotation of the head relative to the stem about the axis defined by the pole 32 and the center of the head 30.

Figure 5:
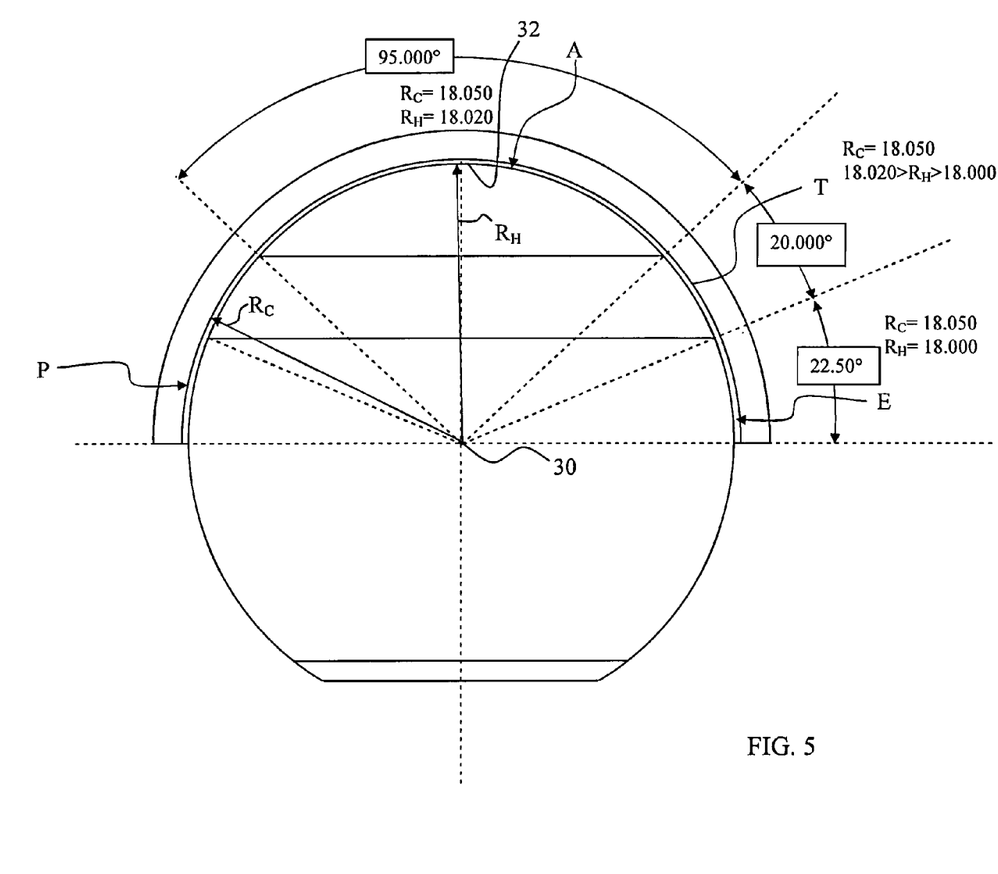
FIG. 5 shows another exemplary embodiment of the femoral head and cup arrangement of FIG. 4 wherein the radius of curvature of the femoral head varies within the transition zone.

FIGS. 5-9 show several other exemplary alternative embodiments of the invention that differ in various ways. In the embodiment of FIG. 5 the head 14 and cup 12 are identical to that of FIG. 4, but the radius of curvature $R_H$ in the transition zone varies between a maximum and a minimum amount. In particular, the radius of curvature $R_H$ gradually transitions in FIG. 5 from 18.020 mm at the perimeter of the articulation zone A to 18.000 mm at the perimeter of the equatorial zone E. Such gradual transition may take the form of a substantially continuous decrease such that $R_H$ transitions in a linear fashion across the transition zone T from a larger radius to a smaller radius. Accordingly, the transition zone T provides a gradually increasing clearance allowing for a smooth transition between the minimum clearance of the prosthesis in the articulation zone A and the maximum clearance of the prosthesis in the equatorial zone E.

Figure 6:
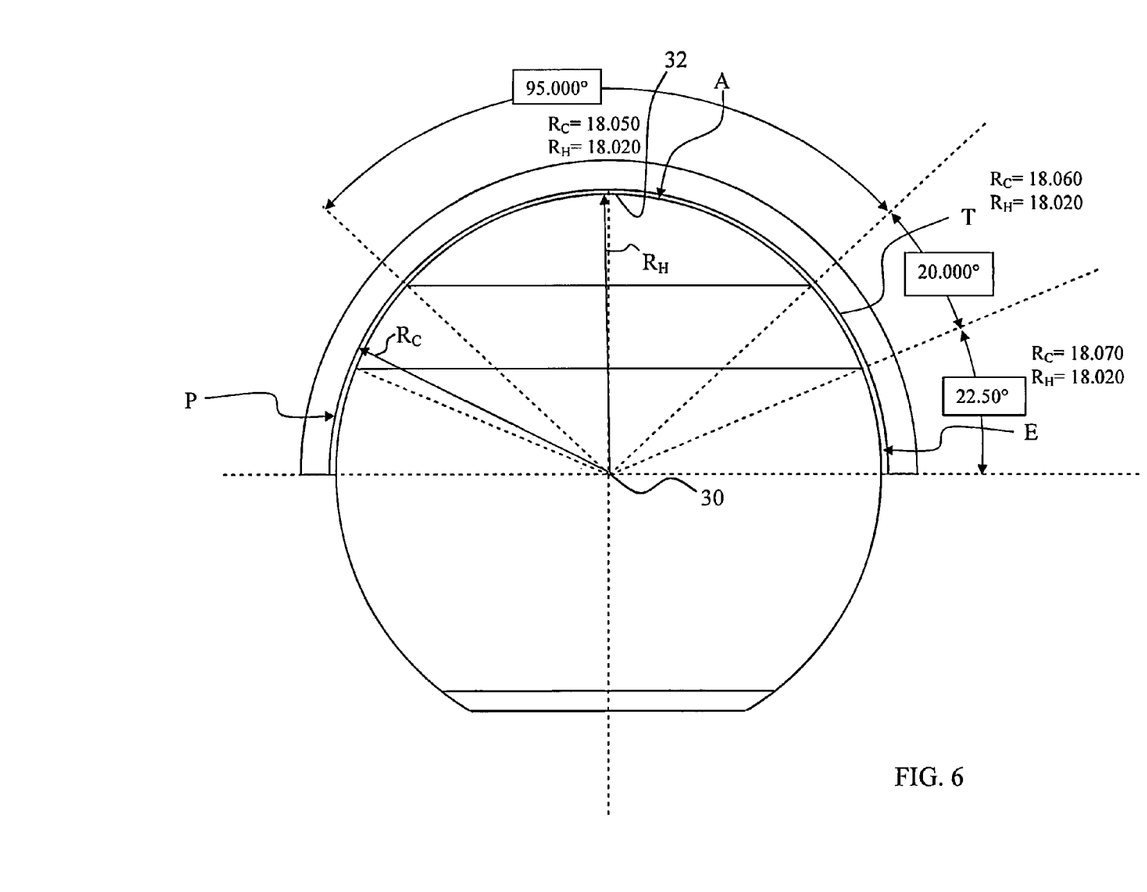
FIG. 6 shows an exemplary embodiment of the femoral head and cup arrangement of FIG. 3 wherein the radius of curvature of the acetabular cup changes from zone to zone and the femoral head is spherical.

FIG. 6 shows an embodiment where the cup 12 provides an aspheric surface and the head 14 provides a generally spherical surface. In this embodiment, the radius of curvature $R_H$ of the head remains 18.020 mm from zone to zone. However, the radius of curvature $R_C$ of the cup changes from zone to zone. In particular, $R_C$ is 18.050 mm in the articulation zone A, 18.060 mm in the transition zone T, and 18.070 mm in the equatorial zone E.

Figure 7:
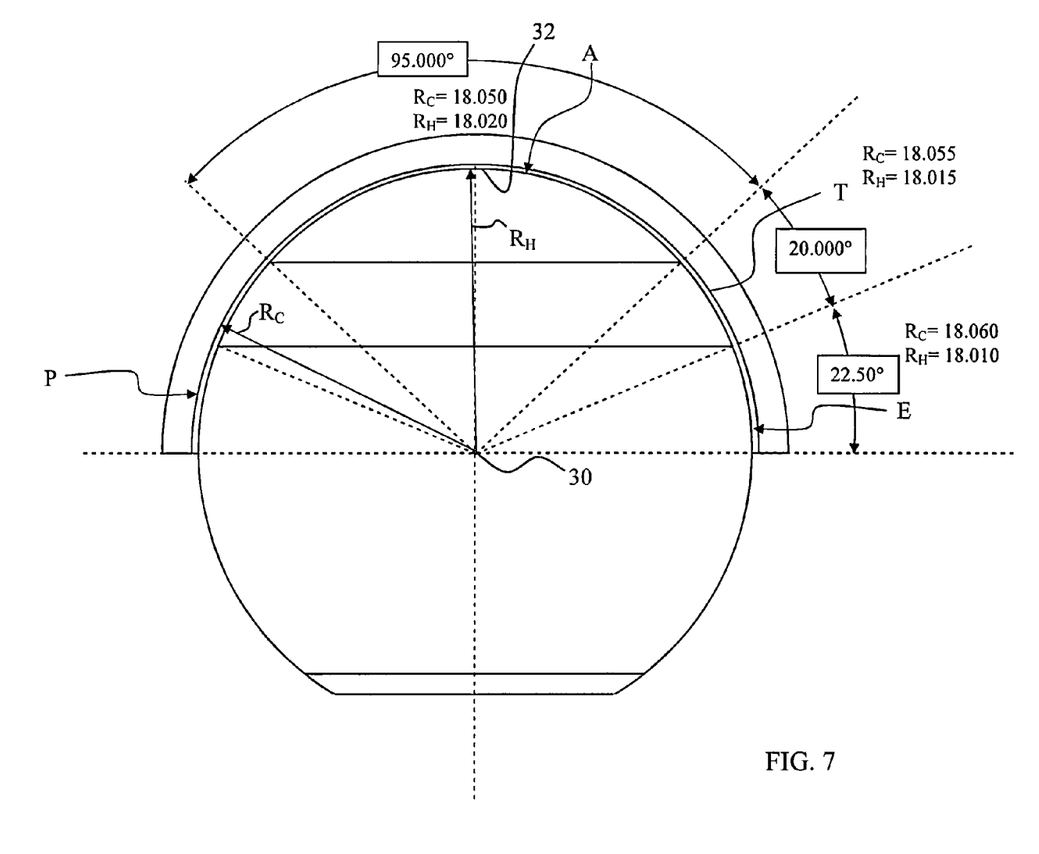
FIG. 7 shows an exemplary embodiment of the femoral head and cup arrangement of FIG. 3 wherein the radius of curvature of both the acetabular cup and the femoral head changes from zone to zone.

FIG. 7 shows an embodiment where the cup 12 and head 14 are both aspheric. In this embodiment, the radius of curvature $R_H$ of the head decreases from 18.020 mm in the articulation zone A, to 18.015 mm in the transition zone T, to 18.010 mm in the equatorial zone E. At the same time, the radius of curvature $R_C$ of the cup increases from 18.050 mm in the articulation zone A, to 18.055 mm in the transition zone T, to 18.060 mm in the equatorial zone E. Thus, the embodiment of FIG. 7 provides two aspheric components where the radial clearance between the components is no greater than about fifty microns in any zone, and is about thirty microns in the articulation zone A.

Figure 8:
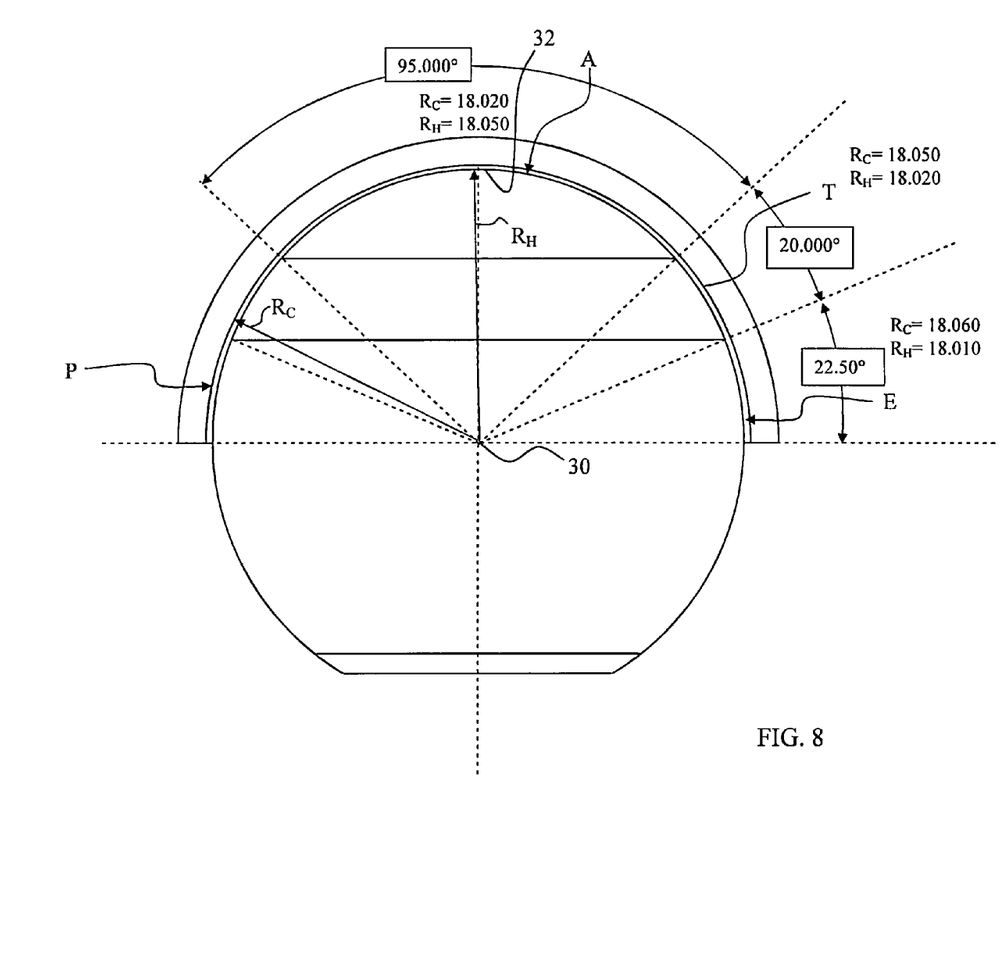
FIG. 8 shows an exemplary embodiment of the femoral head and cup arrangement of FIG. 3 wherein the radius of curvature of the femoral head is greater than the radius of curvature of the acetabular cup in the articulation zone.

FIG. 8 shows an embodiment where the radius of curvature $R_C$ of the cup 12 is actually less than the radius of curvature $R_H$ of the head 12 in the articulation zone A. In particular, $R_C$ is 18.020 mm and $R_H$ is 18.050 microns. Outside of the articulation zone A, the radius of curvature $R_C$ of the cup 12 is greater than the radius of curvature $R_H$ of the head 14. With this arrangement, the cup is configured to receive the head, and even though $R_C$ is less than $R_H$ in the articulation zone, the radial clearance within the articulation zone remains about thirty microns. Outside of the articulation zone, the radial clearance is between about thirty and fifty microns.

Figure 9:
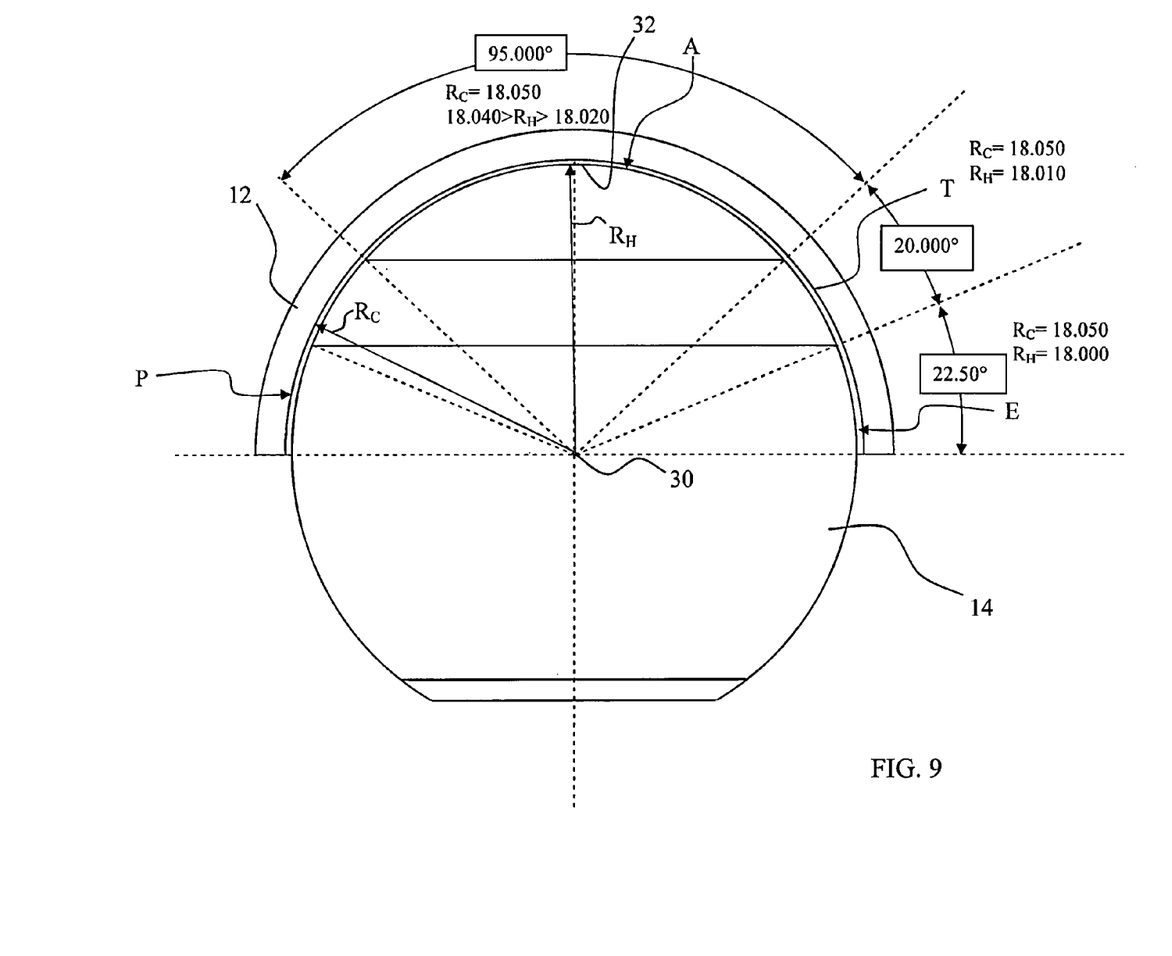
FIG. 9 shows an exemplary embodiment of the femoral head and cup arrangement of FIG. 3 wherein the clearance in the articulation zone is variable.

FIG. 9 shows yet another exemplary embodiment of the joint prosthesis 10. In this embodiment, the clearance in the articulation zone A is variable, similar to the variable clearance described above for the transition zone in the exemplary embodiment of FIG. 5. In FIG. 9, the clearance in the articulation zone is smallest near the pole 32 and the clearance increases when moving from the pole toward the peripheral zone. For example, the radial clearance near the pole may be about ten microns, while the radial clearance near the peripheral zone may be about thirty microns. In FIG. 9, the radius of curvature $R_C$ of the cup 12 is constant at 18.050 mm from zone to zone. Near the pole 32, the radius of curvature $R_H$ of the head 14 is about 18.040. That radius of curvature $R_H$ gradually decreases moving from the pole 32 to the perimeter 44 of the articulation zone A. For example, the radius of curvature $R_H$ of the head may decrease in a linear fashion from 18.040 mm to 18.020 mm with each incremental degree of movement from the pole 32 to the perimeter 44 of the articulation zone A. In the disclosed embodiment of FIG. 9, the radius of curvature $R_H$ of the head further decreases in the transition zone and in the equatorial zone. Of course, one of skill in the art will recognize that this radius of curvature $R_H$ in these zones need not be constant, but may also decrease in a linear or non-linear fashion moving toward the outer edge of the peripheral zone P.

Although the present invention has been described with respect to certain preferred embodiments, it will be appreciated by those of skill in the art that other implementations and adaptations are possible. For example, although FIGS. 4-9 provide several exemplary embodiments where the articulation zone spans 95°, in various alternative embodiments, the articulation zone may span a different angular amount, either less than or more than 95°. Similarly, while the transition zone spans 20°, and the equatorial zone spans 22.5° in the examples of FIGS. 4-9, the span of these zones may also differ in various alternative embodiments. Furthermore, the while exemplary radii of curvature have been shown in FIGS. 4-9, one of skill in the art will recognize that the head and cup are not limited to these radii of curvature, and numerous other radii of curvature may be used to implement the aspheric hip bearing couple described herein. Moreover, there are advantages to individual advancements described herein that may be obtained without incorporating other aspects described above. Therefore, the spirit and scope of the appended claims should not be limited to the description of the preferred embodiments contained herein.

What is claimed is

1. A prosthetic device comprising:
   a cup including a concave cup surface, the concave cup surface defined by at least one radius of curvature $R_C$;
   a head configured to fit within the cup, the head including a convex head surface configured to engage the concave cup surface, the convex head surface defined by at least one radius of curvature $R_H$;
   an articulation zone provided upon the convex head surface, the head surface configured to engage the cup surface in the articulation zone, wherein $R_C$ differs from $R_H$ in the articulation zone by a first amount that is no greater than forty microns; and
   a peripheral zone provided on the convex head surface outside of the articulation zone, wherein $R_C$ differs from $R_H$ in the peripheral zone by a second amount that is greater than the first amount but is no greater than fifty microns, and wherein the peripheral zone extends over an area subtended by a peripheral zone angle of at least 10°, the peripheral zone angle having a vertex at a center of the head.

2. The prosthetic device of claim 1 wherein the articulation zone extends over a region subtended by an articulation zone angle of at least 45° but no greater than 145°, the articulation zone angle having a vertex at the center of the head.

3. The prosthetic device of claim 2 wherein the articulation zone angle is 95°.

4. The prosthetic device of claim 1 wherein the articulation zone is centered about a pole of the head.

5. The prosthetic device of claim 1 wherein the peripheral zone includes a transition zone and an equatorial zone, the transition zone adjacent to the articulation zone and the equatorial zone adjacent to the transition zone.

6. The prosthetic device of claim 5 wherein the second amount gradually increases in the transition zone moving from the articulation zone to the equatorial zone.

7. The prosthetic device of claim 6 wherein the second amount increases in the transition zone in a linear fashion moving from the articulation zone to the equatorial zone.

8. The prosthetic device of claim 6 wherein the second amount remains substantially constant in the equatorial zone moving away from the transition zone.

9. The prosthetic device of claim 5 wherein the transition zone extends over an area subtended by a transition zone angle of at least 10° but no greater than 30°, the transition zone angle having a vertex at the center of the head.

10. The prosthetic device of claim 5 wherein the equatorial zone extends to at least an equator of the head.

11. The prosthetic device of claim 1 wherein $R_C$ remains substantially constant in regions of the concave cup surface opposing the articulation zone and the peripheral zone.

12. The prosthetic device of claim 1 wherein $R_H$ remains substantially constant in the articulation zone and the peripheral zone.

13. The prosthetic device of claim 1 wherein $R_H$ is greater in the articulation zone than the peripheral zone.

14. The prosthetic device of claim 1 wherein $R_C$ is lesser in regions of the concave cup surface opposing the articulation zone than in regions of the concave cup surface opposing the peripheral zone.

15. The prosthetic device of claim 1 wherein $R_C$-$R_H$ is greater than zero in the articulation zone and in the peripheral zone.

16. The prosthetic device of claim 1 wherein the transition zone is adjacent to the articulation zone.

17. A prosthetic device comprising:
a cup including a concave cup surface, the concave cup surface defined by at least one radius of curvature $R_C$;
a head configured to fit within the cup, the head including a convex head surface configured to engage the concave cup surface, the convex head surface defined by at least one radius of curvature $R_H$;
an articulation zone provided on the convex head surface, the convex head surface configured to engage the concave cup surface in the articulation zone, wherein $R_C$ differs from $R_H$ in the articulation zone by a first radial clearance, wherein the first radial clearance is no greater than fifty microns;
a peripheral zone provided on the convex head surface outside of the articulation zone, wherein $R_C$ differs from $R_H$ in the peripheral zone by a second radial clearance that is greater than the first radial clearance; and
wherein the first radial clearance gradually increases in the articulation zone from a lesser radial clearance near a pole of the head to a greater radial clearance near the peripheral zone.

18. The prosthetic device of claim 17 wherein the first radial clearance increases in a linear fashion in the articulation zone from the lesser clearance near the pole of the head to the greater radial clearance near the peripheral zone.

19. A prosthetic device comprising:
a cup including a concave cup surface, the concave cup surface defined by at least one radius of curvature $R_C$;
a head configured to fit within the cup, the head including a convex head surface configured to engage the concave cup surface, the convex head surface defined by at least one radius of curvature $R_H$;
wherein the convex head surface provides an articulation zone where the head surface engages the cup surface, wherein $R_C$ differs from $R_H$ in the articulation zone by a first amount that is less than fifty microns, and wherein the articulation zone extends over a first area subtended by a first angle between 85° and 105°, the first angle having a vertex at a center of the head;
wherein the convex head surface provides a transition zone adjacent the articulation zone, wherein $R_C$ differs from $R_H$ in the transition zone by a second amount that is greater than the first amount but is no greater than fifty microns, and wherein the transition zone extends over an area subtended by a second angle of at least 10°, the second angle having a vertex at the center of the head; and
wherein the convex head surface provides an equatorial zone adjacent the transition zone such that the transition zone lies between the articulation zone and the equatorial zone, wherein $R_C$ differs from $R_H$ in the equatorial zone by a third amount that is greater than the first amount and the second amount but is no greater than fifty microns, and wherein the equatorial zone extends over an area subtended by a third angle of at least 10°, the third angle having a vertex at the center of the head.

20. The prosthetic device of claim 19 wherein the second amount gradually increases in the transition zone when moving toward the equatorial zone.

* * * * *